(12) United States Patent
Chiu

(10) Patent No.: US 6,972,117 B2
(45) Date of Patent: Dec. 6, 2005

(54) APPARATUS FOR PRODUCING OZONE GAS FOR BEAUTY TREATMENT

(75) Inventor: Chun Kwok Sanny Chiu, Kowloon (CN)

(73) Assignee: Newford Company Limited, Kowloon (CN)

( * ) Notice: Subject to any disclaimer, the term of this patent is extended or adjusted under 35 U.S.C. 154(b) by 210 days.

(21) Appl. No.: 10/473,658

(22) PCT Filed: Jun. 13, 2002

(86) PCT No.: PCT/GB02/02749

§ 371 (c)(1),
(2), (4) Date: Sep. 30, 2003

(87) PCT Pub. No.: WO02/100774

PCT Pub. Date: Dec. 19, 2002

(65) Prior Publication Data

US 2004/0105793 A1    Jun. 3, 2004

(30) Foreign Application Priority Data

Jun. 13, 2001  (GB) .................................. 0114428

(51) Int. Cl.⁷ .............................................. B01J 19/08
(52) U.S. Cl. ......................... 422/186.07; 422/186.08; 422/186.21
(58) Field of Search ...................... 422/186.07, 186.08, 422/186.21

(56) References Cited

U.S. PATENT DOCUMENTS

| 2,745,407 A | 5/1956 | Mueller et al. ............. 128/407 |
| 5,866,082 A | 2/1999 | Hatton et al. .......... 420/186.07 |

FOREIGN PATENT DOCUMENTS

| CN | 1235813 A | 11/1999 | .......... A61B 17/36 |
| DE | 36 18 412 A1 | 12/1987 | ............ A61N 1/44 |
| GB | 2 203 618 A | 10/1988 | ........... C01B 13/11 |

OTHER PUBLICATIONS

International Search Report of PCT/GB02/02749, dated Oct. 8, 2002.
English translation of IPER for International Application No. PCT/GB02/02749, dated Sep. 22, 2003.

*Primary Examiner*—Steven Versteeg
(74) *Attorney, Agent, or Firm*—Christie, Parker and Hale, LLP

(57) ABSTRACT

Apparatus for producing ozone gas for use in the beauty treatment of skin, comprising a sealed vessel (1) containing a gas and means for supplying to the vessel a potential difference (9), thereby causing the gas to become charged, whereby placing the vessel close to the skin of a user causes the charged gas to discharge by creating an electrical spark which jumps between the vessel and the skin, the spark resulting in the production of ozone gas in the vicinity of the skin, wherein the apparatus additionally comprises a guard (1a) for the vessel to protect the vessel from breakage, the guard having apertures therein to permit the vessel to discharge to the skin of the user.

2 Claims, 1 Drawing Sheet

Figure 1:
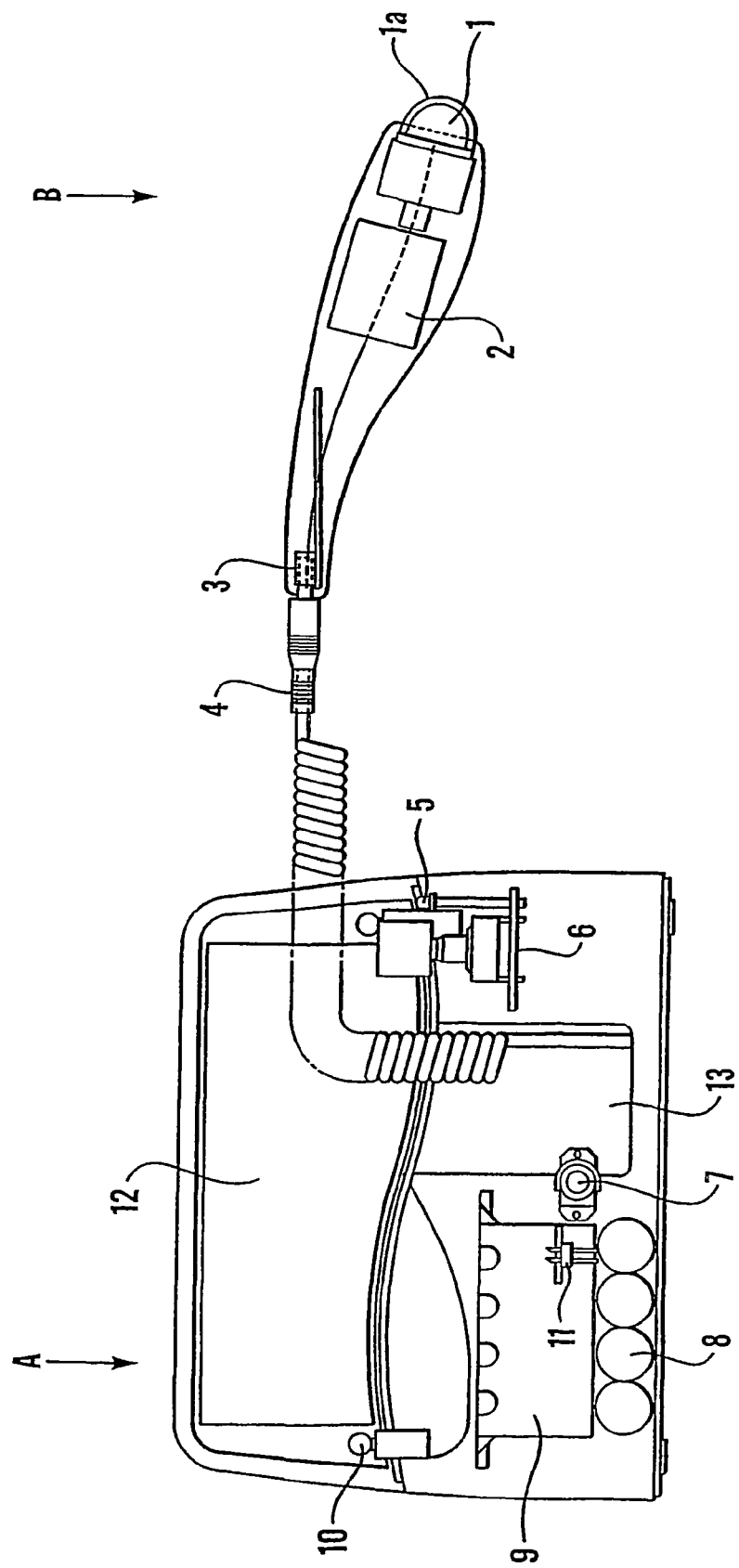

APPARATUS FOR PRODUCING OZONE GAS FOR BEAUTY TREATMENT

CROSS-REFERENCE TO RELATED APPLICATION

This application is a National Phase Patent Application of International Application Number PCT/GB02/02749, filed on Jun. 13, 2002, which claims priority of British Patent Application Number 0114428.6, filed on Jun. 13, 2001.

The present invention relates to apparatus for producing ozone gas for use in the beauty treatment of skin, and in particular to apparatus which can be used to treat skin blemishes.

Skin blemishes can be treated by applying ozone gas to the skin. One method of producing ozone is by discharging a charged object close to the skin. This generates electrical sparks which ionise the oxygen in the vicinity of the skin, thereby producing ozone gas.

U.S. Pat. No. 5,866,082 (Omega 5 Technologies Inc.) discloses a hand-held ozone-producing apparatus having a glass bulb filled with an inert gas such as neon, which is charged and discharged using a pair of capacitors in order to produce electrical sparks between the glass bulb and the user's skin in order to create ozone. It is admitted in U.S. Pat. No. 5,866,082 that the exposed portion of the glass bulb is likely to break. The invention is the isolation of electrically live components so that the user cannot come into contact with those components even when the bulb is broken. When the bulb breaks, the neon gas escapes, and the bulb is no longer able to conduct electrical energy in order to produce a spark.

Clearly, it would be better if an ozone-producing apparatus could be provided in which the bulb did not break at all.

In accordance with a first aspect of the present invention, there is provided apparatus for producing ozone gas for use in the beauty treatment of skin, comprising a sealed vessel containing a gas and means for supplying to the vessel a potential difference, thereby causing the gas to become charged, whereby placing the vessel close to the skin of a user causes the charged gas to discharge by creating an electrical spark which jumps between the vessel and the skin, the spark resulting in the production of ozone gas in the vicinity of the skin, wherein the apparatus additionally comprises a guard for the vessel to protect the vessel from breakage, the guard having apertures therein to permit the vessel to discharge to the skin of the user.

The technical advantage of the present invention is that the guard protects the vessel (which is preferable made from glass) from impact whilst not preventing normal functioning of the apparatus.

Preferably, the outer surface of the guard is a constant distance from the bulb, most preferably from 1–2 mm, such that the skin of the user is kept a constant distance from the bulb when it contacts any part of the guard. This results in a constant effect of the device upon the user's skin.

The guard is preferably formed from an electrical insulator such as a plastics material.

A preferred embodiment of the present invention will now be described, with reference to the drawings, in which:

FIG. 1 shows a schematic diagram, in partial cross section, of ozone-producing apparatus in accordance with the invention.

The apparatus comprises housing A and hand-held pen B, which can be operated in the vicinity of the user's skin and from which the ozone is produced.

Pen B comprises gas bulb 1 which is a sealed unit containing neon gas. Part of bulb 1 emerges from the housing of pen B, and this exposed part is protected by plastic gas bulb guard 1a, which partially covers bulb 1 but which has holes therein (not shown) to allow sparks to emanate from bulb 1 and contact the user's skin. The arrangement of guard 1a is such that it prevents bulb 1 from getting closer than 2 mm from the user's skin. It will be understood that this distance can be adjusted based on the spacing of guard 1a around bulb 1 when guard 1a is constructed.

Bulb 1 is electrically connected to a self coupling high voltage transformer 2, which is itself connected to electrical pulse producer 9 in housing A by means of DC spring coil cable 4. Cable 4 connects pen B to housing A via connecting jack 3, and can be stored in cable recess 13 when not in use. Pulse producer 9 is powered either by rechargeable batteries 8 or by external power via DC jack 7. LED indicator 5 provides information about the functioning of the apparatus, as will be described below.

The functioning of the apparatus is controlled by means of control device 6. This consists of two different control means. The first is an intensity control, which adjusts the output frequency of the pulse producer in order to control the maximum and minimum intensities of ozone released from bulb 1. The second comprises a timer control which allows the user to produce ozone constantly for a predetermined treatment time of between 1 and 5 minutes. When the time has elapsed, the apparatus shuts down automatically.

Mirror 12 is adjustable on hinge 10 to allow the user to see the region of skin which is being treated (such as the face).

In operation, pulse producer 9 generates a pulse type constant voltage with a peak value of at least 100 volts and an oscillation frequency and pulse width of approximately 200 Hz and 50 microseconds respectively. This pulse voltage is applied to self-coupling high voltage transformer 2 along DC spring coil cable 4. Transformer 2 boosts the supplied pulse voltage in order to produce a high frequency and bi-polar pulsing high voltage with a peak value of at least 9000 volts and a frequency of approximately 250 kHz. This voltage is applied to gas bulb 1 by means of an electrode connecting transformer 2 and gas bulb 1. The result is ignition of the neon gas inside the bulb to become a conductive gas.

In order to treat the user, pen B is brought close to the skin of the user until gas bulb guard 1a contacts the skin. This means that bulb 1 comes within 2 mm from the user's skin. Because the user's skin is at an earth potential with respect to gas bulb 1, gas bulb 1 discharges into the user's skin by means of a so-called "corona" effect. Electrons present in the gap between gas bulb 1 and the skin are accelerated by means of an electron avalanching effect. Oxygen molecules in the air which come into contact with the accelerating electrons are ionised to generate ozone in the vicinity of the user's skin by means of a chain reaction. The holes in guard 1a allow sparks and ozone molecules to impinge upon the user's skin even when guard 1a is in contact with the skin. Clearly, the number and position of the holes can be varied in order to control the intensity of effect.

In order to keep a constant ozone generation, pulse producer 9 generates a constant output voltage which is boosted continually by self-coupling transformer 2.

LED indicator 5 is a bi-colour LED which can glow one colour to show that the apparatus is functioning correctly, and another colour to show that rechargeable batteries 8 are being charged.

What is claimed is:

1. Apparatus for producing ozone gas for use in the beauty treatment of skin, comprising a sealed vessel containing a gas and means for supplying to the vessel a potential difference, thereby causing the gas to become charged, whereby placing the vessel close to the skin of a user causes the charged gas to discharge by creating an electrical spark which jumps between the vessel and the skin, the spark resulting in the production of ozone gas in the vicinity of the skin, the apparatus additionally comprising a guard for the vessel to protect the vessel from breakage, the guard having apertures therein to permit the vessel to discharge to the skin of the user wherein the guard is formed from an electrical insulator and wherein the outer surface of the guard is a constant distance from the bulb, such that the skin of the user is a constant distance from the bulb when it contacts any part of the guard.

2. Apparatus as claimed in claim 1, wherein said distance is from 1–2 mm.

* * * * *